US005658572A

United States Patent [19]
Paoletti et al.

[11] Patent Number: 5,658,572
[45] Date of Patent: Aug. 19, 1997

[54] INFECTIOUS BURSAL DISEASE VIRUS RECOMBINANT POXVIRUS VACCINE

[75] Inventors: Enzo Paoletti, Delmar; Jill Taylor, Albany, both of N.Y.

[73] Assignee: Virogenetics Corporation, Troy, N.Y.

[21] Appl. No.: 204,729

[22] Filed: Feb. 28, 1994

Related U.S. Application Data

[63] Continuation of Ser. No. 736,254, Jul. 26, 1991, abandoned.

[51] Int. Cl.$^6$ .................... A61K 39/275; A61K 39/295; A61K 39/12; C12N 7/01
[52] U.S. Cl. .................... 424/199.1; 435/235.1; 435/320.1; 424/204.1; 424/232.1; 935/65
[58] Field of Search .................... 435/235.1, 69.1, 435/69.3, 91, 172.3, 240.1, 320.1; 424/199.1, 204.1, 232.1; 536/23.1, 23.72; 935/9, 32, 34, 57, 65, 70

[56] References Cited

U.S. PATENT DOCUMENTS

| | | | |
|---|---|---|---|
| 5,174,993 | 12/1992 | Paoletti | 424/89 |
| 5,364,773 | 11/1994 | Paoletti et al. | 435/69.1 |

FOREIGN PATENT DOCUMENTS

| | | | |
|---|---|---|---|
| 89/01040 | 2/1989 | WIPO | C12N 15/00 |

OTHER PUBLICATIONS

Heine, H.-G. et al. Virus Research, vol. 32, pp. 313–328 1994.
Heine, H.-G. et al. Archives of Virology, vol. 131, pp. 277–292 1993.
Azad et al Vaccines 90 pp. 59–62 (1990) Cold Spring Harbor Laboratory Press, CSH, NY.
Oppling et al., Jnl. Gen. Virol. 72: 2275–2278 (1991).
Oppling et al., Arch. Virol. 119: 211–223 (1991).
Bayliss et al., Arch. Virol. 120: 193–205 (1991).
Bayliss et al., Jrnl. Gen. Virol. 71: 1303–1312 (1990).
Heine et al., Jrnl. Gen. Virol. 72:1835–1843 (1991).
Azad et al., Vaccine 9:715–22 (1991).
Fahey et al., Avian Diseases 35:365–73 (1991).
Jagadish et al., Virology 184:805–07 (1991).
Allan, W.H., J.T. Faragher, and G.A. Cullen, Vet. Rec. 90, 511–512 (1972).
Azad, A.A., S.A. Barrett, and K.J. Fahey, Virology 143, 35–44 (1985).
Azad, A.A., K.J. Fahey, S. Barrett, K. Erny and P. Hudson, Virology 149, 190–198 (1986).
Azad, A.A., M.N. Jagadish, M.A. Brown, and P.J. Hudson, Virology 161, 145–152 (1987).
Baxendale, W. and Lutticken, Dev. Biol. Stand. 51, 211–219 (1981).
Becht, H., H. Muller, and H.K. Muller, J. Gen. Virol. 69, 631–640 (1988).
Brown, F., Intervirology 25, 141–143 (1986).
Burkhardt, E. and H. Muller, Archives of Virology 94, 297–303 (1987).
Clewell, D.B., J. Bacteriol. 110, 667–676 (1972).

Clewell, D.B. and D.R. Helinski, Proc. Natl. Acad. Sci. USA 62, 1159–1166 (1969).
Dobos, P., J. Virol. 32, 1046–1050 (1979).
Dobos, P., B.J. Hill, R. Hallett, D.T. Kells, H. Becht, and D. Teninges, J. Virol. 32, 593–605 (1979).
Duncan, R., E. Nagy, P.J. Krell and P. Dobos, J. Virol. 61, 3655–3664 (1987).
Edbauer, C., R. Weinberg, J. Taylor, A. Rey–Senelonge, J.F. Bouquet, P. Deamettre and E. Paoletti, Virology 179, 901–904 (1990).
Fahey, K.J., I.J. O'Donnell, and A.A. Azad, J. Gen Virol. 66, 1479–1488 (1985a).
Fahey, K.J., I.J. O'Donnell, and T.J. Bagust, J. Gen. Virol. 66, 2693–2702 (1985b).
Fahey, K.J., K. Erny and J. Crooks, J. Gen. Virol. 70, 1473–1481 (1989).
Guo, P., S. Goebel, S. Davis, M.E. Perkus, B. Languet, P. Desmettre, G. Allen, and E. Paoletti, J. Virol. 63, 4189–4198 (1989).
Hudson, P.J., N.M. McKern, B.E. Power, and A.A. Azad, Nucl. Acids. Res. 14, 5001–5012 (1986).
Jackwood, D.J., Y.M. Saif, and J.H. Hughes, Avian Dis. 28, 990–1006 (1984).
Jagadish, M.N., V.J. Staton, P.J. Hudson, and A.A. Azad, J. Virol. 62, 1084–1087 (1988).
Kaufer, I. and E. Weiss, Infect. Immun. 27, 364–367 (1980).
Kibenge, F.S.B., A.S. Dhillon, and R.G. Russell, J. Gen. Virol. 69, 1757–1775 (1988).
Ley, D.H., R. Yamamoto, and A.A. Bickford, Avian Diseases 23, 219–224 (1979).
Lucio, B. and S.B. Hitchner, Avian Dis. 23, 466–478 (1979).
Lukert, P.D. and S.B. Hitchner, In Diseases of Poultry 8th edition, eds. M.S. Hofstad, H.J. Barnes, B.W. Calnek, W.M. Reid and H.W. Yoder (Iowa State University Press–Ames) pp. 566–576 (1984).
Lukert, P.D. and L.A. Mazariegos, J. Am. Vet. Med. Assoc. 187, 306 (Abstr).
Lukert, P.D. and Y.M. Saif, In Diseases of Poultry 9th edition, eds. B.W. Calnek, H.J. Barnes, C.W. Beard, W.M. Reid and H.W. Yoder (Iowa State University Press–Ames) pp. 648–663 (1991).
Macreadie, I.G., P.R. Vaughan, A.J. Chapman, N.M. McKern, M.N. Jagadish, H.G. Heine, C.W. Ward, K.J. Fahey, and A.A. Azad, Vaccine 8, 549–552 (1990).
Matthews, R.E.F., Intervirology 17, 42–44 (1982).
McFerran, J.B., M.S. McNulty, E.R. McKillop, T.J. Connor, R.M. McCracken, D.S. Collins, and G.M. Allan, Avian Pathol. 9, 395–404 (1980).
McNulty, M.S. and Y.M. Saif, Avian Dis. 32, 374–375 (1988).

(List continued on next page.)

Primary Examiner—Mary E. Mosher
Attorney, Agent, or Firm—Curtis Morris & Safford P.C.

[57] ABSTRACT

What is described is a recombinant poxvirus, such as fowlpox virus, containing foreign DNA from infectious bursal disease virus. What is also described is a vaccine containing the recombinant poxvirus for inducing an immunological response in a host animal inoculated with the vaccine.

10 Claims, 3 Drawing Sheets

OTHER PUBLICATIONS

Muller, H., Arch. Virol. 87, 191–203 (1986).
Muller, H. and H. Betch, J. Virol. 44, 384–392 (1982).
Nagy, E., R. Duncan, P. Krell, and P. Dobos, Virology 158, 211–217 (1987).
Panicali, D. and E. Paoletti, Proc. Natl. Acad. Sci. USA 79, 4927–4931 (1982).
Perkus, N.E., K. Limbach, and E. Paoletti, J. Virol. 63, 3829–3836 (1989).
Piccini, A., M.E. Perkus, and E. Paoletti, In Methods in Enzymology, vol. 153, eds. Wu, R., and Grossman, L., (Academic Press) pp. 545–563 (1987).
Schat, K.A., B. Lucio, and J.C. Carlisle, Avian Dis. 25, 996–1004 (1981).
Skeeles, J.K., P.D. Lukert, E.V. De Buysscher, O.J. Fletcher, and J. Brown, Avian Dis. 23, 95–106 (1979).
Snyder, D.S., D.P Lana, B.R. Cho, and W.W. Marquardt, Avian Dis. 32, 527–534 (1988).
Spies, U., H. Muller, and H. Becht, Virus Res. 8, 127–140 (1987).
Taylor, J., C. Edbauer, A. Rey–Senelonge, J.F. Bouquet, E. Norton, S. Goebel, P. Desmettre and E. Paoletti, J. Virol. 64, 1441–1450 (1990).
Taylor, J., R. Weinberg, Y. Kawaoka, R. Webster and E. Paoletti, Vaccine 6, 504–508 (1988).
Winterfield, R.W., A.S. Dhillon, H.L. Thacker, L.J. Alby, Avian Dis. 24, 179–188 (1980).

```
          10        20        30        40        50        60        70        80        90       100
GATATCTGTGGTCTATATATACTACACCCTACCGATATTAACCAACGAGTTTCTCACAGAAAAACTTGTTTAGTAGATAGAGATTCTTTGATTGTGTTTA 110       120       130       140       150       160       170       180       190       200
AAAGAAGTACCAGTAAAAAGTGTGGCATATGAGAAAATAAACAAAAACATATTTCCGAACAGTATTTTGGAATTCTCCCAAGTTGTAAACATAT 210       220       230       240       250       260       270       280       290       300
TTTTTGCCTATCATGTATAAGACGTTGGGCAGATACTACCAGAAATACTGAAAATACGTGTCCTGAATGTAGAATAGTTTTCCTTTCATAATA 310       320       330       340       350       360       370       380       390       400
CCCAGTAGGTATTGGATAGATAATAAAATATGATAAAAAAATATTATATAATAGATATAAGAAAATAACCTATAAGAACAATAAAA 410       420       430       440       450       460       470       480       490       500
ATATAATTACATTTACGGAAAATAGCTGGTTTTACCAACTTAGAGTAATTATCATATTGAATCTATATTGTTTTTAGTTATATAAAAACATGAT 510       520       530       540       550       560       570       580       590       600
TAGCCCCCAATCGGATGAAAATATAAAAGATGTTGAGAATACAACAAAAAGAGGAATCGTACGTTGTCCATATCCAAACATATAATAAAAAT 610       620       630       640       650       660       670       680       690       700
TCAAAAGTAGTATTATACTGGATGTTTAGAGATCAACGTGTACAAGATAATTGGGCTTTAATTTACGCACAACGATTAGGTTAAAACTCAAAATACCTC 710       720       730       740       750       760       770       780       790       800
TAAGAATATGCTTTTGTGTCGTGCCAAAATTCACACTACTTCTAGACACTTTATGTTTTTTAATATCCGGTCTTAAAGAAGTCGCGGAAGAATGTA 810       820       830       840       850       860       870       880       890       900
AAAGACTATGTATAGGGTTTTCATTGATATATGGGCGTACCAAAAGTAATAATTCCGTGTATAGTAAAAAATACAGAGTCGGAGTAATCATAACGGATTT 910       920       930       940       950       960       970       980       990      1000
CTTTCCATTACGTTCCGGAAAGATTAATGAAACAGACTGTAATATCTCTTCCAGATAACACTACCTTTTATACAAGTAGACGCTCATAATATAGTACCT 1010      1020      1030      1040      1050      1060      1070      1080      1090      1100
TGTTGGGAAGCTTCTGATAAGAAGAATACGGTGCACGAACTTTAAGAAAAAGATATTTGATAAATTATATGAATATGACAGAATTTCCTGTGTTC 1110      1120      1130      1140      1150      1160      1170      1180      1190      1200
GTAAACATCCATACGGTCCATTTTTCTATATCTATTGCAAAAACCCAAAAACAGATTAGACAAGAGGGTATTACCGTAAAATGGGCAACGCCTGGAAC 1210      1220      1230      1240      1250      1260      1270      1280      1290      1300
AAAAGCTGGAATAATTGTTTAAAAGAATTTATAAAAAACAGATTACGACGCGGATCATAACAATCCTACGTGTGACGCTTTGAGTAACTTA
```

FIG. 1A

```
      1310       1320       1330       1340       1350       1360       1370       1380       1390       1400
TCTCCGTGGCTACATTTGGTCATGTATCCGCACAACGTGTTGCCTTAGAAGTATTAAATGTATACGAGAAAGCAAAAAAACGTTGAAACGTTTATAG 1410       1420       1430       1440       1450       1460       1470       1480       1490       1500
ATGAAATAATTGTAAGAAGAACTATCGGATAATTTTGTTACTATAACAAACATTATGATAGTATCCAGTCTACTCATTCATGGGTTAGAAAAACATT 1510       1520       1530       1540       1550       1560       1570       1580       1590       1600
AGAAGATCACATTAATGATCCTAGAAAAGTATATATATTCCATTAAACAACTCGAAAAAGCGGAAACTCATGATCCTCTATGGAACGCGTCACAAATGCAG 1610       1620       1630       1640       1650       1660       1670       1680       1690       1700
ATGGTGAGAGAAGGAAAAATGCATAGTTTTTTACGAATGTATTGGGCTAAGAAGATACTTGATGGACTAGAACACCTGAAGACGCTTTGAGTTATAGTA 1710       1720       1730       1740       1750       1760       1770       1780       1790       1800
TCTATTTGAACAACAGTACGAACTAGACGGCACGGATCCTAACGGATCGTAGGTTGTATGTGGTCTATTTGCGGATTACACGATAGAGCGTGGAAAGC 1810       1820       1830       1840       1850       1860       1870       1880       1890       1900
AAGACCGATATTTGGAAGATAAGATATGAGAGTTCTAAGAAGAAATTTGATGTTGCTGTATTTATACAGAAATACAATTAAGATAAATAA 1910       1920       1930       1940       1950       1960       1970       1980       1990       2000
TATACAGCATTGTAACCATCGTTATCCGTTATACGGGGAATAATATTACCATACAGTATTATTAAATTTCTTACGAAGAATATAGATCGGTATTTATCG 2010       2020       2030       2040       2050       2060       2070       2080       2090       2100
TTAGTTTATTTTTACATTTATTAATTAAACATGTCTACTATTACCTGTTATGGAAATGACAAATTTAGTTATATAATTTATGATAAAATTAAGATAATAAT 2110       2120       2130       2140       2150       2160       2170       2180       2190       2200
AATGAAATCAAATAATTATGTAAATGCTACTAGATTGTGAATTACGAGGAAGAAATTAAGTTACGAACTTAAGTGAATCTAAAATATTAGTC 2210       2220       2230       2240       2250       2260       2270       2280       2290       2300
GATAATGTAAAAAAAAATAAATGATAAATAACCAGTTAAAAACGGATTATATACGTTAAGGATATATTGATCATAAAGGAAGAGATACTTGCGGTT 2310       2320       2330       2340       2350       2360       2370       2380       2390       2400
ACTATGTACACCAAGATCTGGTATCTTCTATATCAAATTGGATATCTCCGTTATTCGCCGTTAAGGTAAATAAAATTAAACTATTATATGTAATGA 2410       2420       2430       2440       2450       2460       2470       2480       2490       2500
ATATGATATACGACTTAGCGAAATGGAATCTGATATGACAGAAGTAGTTGATAAATTAGTAGGAGGATACAATGATGAAATAGCAGAAATA
```

```
         2510      2520      2530      2540      2550      2560      2570      2580      2590      2600
ATATATTTGTTAATAAATTTATAGAAAAATATATTAAATTTATAGAATTATCGTTATCAACTGAATTATCTAGTATATTAAATAATTTATAAATTTATAAATT 2610      2620      2630      2640      2650      2660      2670      2680      2690      2700
TTAATAAAAATACAATAACGACATAAAGATATTTAATTCTTTGATCTGAAAACACATCTATAAAACTAGATAAAAGTTATTCGATAAAGAT 2710      2720      2730      2740      2750      2760      2770      2780      2790      2800
AATAATGAATCGAACGATGAAAAATTGGAAACAGAAGTTGATAAGCTAATTTTTTCATCTAAATAGTATATTTATTGAAGTACGAAGTTTTACGTTA 2810      2820      2830      2840      2850      2860      2870      2880      2890      2900
GATAAATAATAAAGGTCGATTTTTGTTAAATATCAAATATGTCATTATCTGATAAAGATACAAAAACACACGGTGATTATCAACCATCTAACGAA 2910      2920      2930      2940      2950      2960      2970      2980      2990      3000
CAGATATTACAAAAAAATACGTCGGACTATAGCCTCAATAGAGAAGCTGATAGCCTAATAGAAGAAGCATTAAAGAAATTGTTGTAGATGTTATGAAGAATTGGG 3010      3020      3030      3040      3050      3060      3070      3080      3090      3100
ATCATCCTCAACGAAGAAATAGATAAAGTTCTAAACTGGAAAAATGATACATTAAACGATTTAGATCATCTAAATACAGATGATAATATTAAGGAAATCA 3110      3120      3130      3140      3150      3160      3170      3180      3190      3200
TACAATGTCTGATTAGAGAATTTGCGTTTAAAAAGATCAATTCTATTATGTATAGTTATGCTATGGTAAAACTCAATTCAGATAACGAACATTGAAAGAT 3210      3220      3230      3240      3250      3260      3270      3280      3290      3300
AAAATTAAGGATTATTTTATAGAAAACTATTCTTAAAGACAAAACGTGGTTATAAACAAAAGCCATTACCCGGATTGGAAACTAAAATACTAGATAGTATTA 3310      3320      3330      3340      3350      3360      3370      3380      3390      3400
TAAGATTTTAAAAAACATAAAAATTAATAGGTTTTTATAGATTGACTTATTATTATACAATATGGATAAAGATATATATCAACTAGAAAGTTGAATGACGGA 3410      3420      3430      3440      3450      3460      3470      3480      3490      3500
TTCTTAATTTTATATTATGATTCAATAGAATCATTTGTCATGTCGTAATAGATACTTTAGATAAAATTACGCGTTACTAGCTAAGAAAAACAAGGACTTTA 3510      3520      3530      3540      3550      3560      3570      3580      3590      3600
ATGAATGGCTAAAGATAGAATCATTTAGAGAAATAATAGATACTTAGGACAACGATCTAGGACAACGATATTGTGAAGAACTTACGGGGCA 3610      3620      3630      3640      3650      3660
TCACATTCCAGTGTAATTATTGAGGTCAAAGCTAGTAACTTAATAGATGACAGGACAGCTG
```

INFECTIOUS BURSAL DISEASE VIRUS RECOMBINANT POXVIRUS VACCINE

This application is a continuation of application Ser. No. 07/736,254, filed Jul. 26, 1991, now abandoned.

FIELD OF THE INVENTION

The present invention relates to a modified poxvirus and to methods of making and using the same. More in particular, the invention relates to recombinant poxvirus, which virus expresses gene products of an infectious bursal disease virus (IBDV) gene, and to vaccines which provide protective immunity against IBDV infections.

Several publications are referenced in this application. Full citation to these references is found at the end of the specification preceding the claims. These references describe the state-of-the-art to which this invention pertains.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of the vaccinia virus described in U.S. Pat. No. 4,603,112, the disclosure of which patent is incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell et al., 1969; Sambrook et al., 1989).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

The technology of generating vaccinia virus recombinants has recently been extended to other members of the poxvirus family which have a more restricted host range. The avipox virus, fowlpox, has been engineered as a recombinant virus. This recombinant virus is described in PCT Publication No. WO89/03429.

Fowlpox virus (FPV) has advantageously been engineered as a vector expressing antigens from poultry pathogens. The hemagglutinin protein of a virulent avian influenza virus was expressed in an FPV recombinant (Taylor et al., 1988). After inoculation of the recombinant into chickens and turkeys, an immune response was induced which was protective against either a homologous or heterologous virulent influenza virus challenge (Taylor et al., 1988). In addition, the surface glycoproteins (fusion and hemagglutinin) of a virulent strain of Newcastle Disease Virus have been expressed in an FPV vector and shown to induce a protective immune response (Taylor et al., 1990; Edbauer et al., 1990).

FPV is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of the virus causing a productive infection in any non-avian species including man. This host restriction provides an inherent safety barrier to transmission of the virus to other species and makes use of FPV as a vaccine vector in poultry an attractive proposition.

Infectious bursal disease, also known as Gumboro's disease, manifests itself in two ways. In chickens older than three weeks, infectious bursal disease virus (IBDV) can cause impaired growth and mortality losses of up to 20% (Lukert and Hitchner, 1984). In younger birds, the disease is subclinical but is evident as microscopic lesions in the bursa of Fabricius (Winterfield et al., 1972). This results in prolonged and severe immunosuppression which causes increased susceptibility to disease and interferes with vaccination programs against other disease agents (Allan et al., 1972). Characteristics of the disease have been reviewed in Lukert and Saif (1991) and will be summarized briefly here.

The cloacal bursa appears to be the primary target organ of the virus and birds surgically bursectomized at 4 weeks have been shown to survive a lethal IBDV challenge without clinical manifestations (Kaufer and Weis, 1980). The age of bursectomy is however, critical. Schat et al., (1981) performed embryonal bursectomy and then challenged with IBDV at 2 and 6 weeks of age. Birds developed typical hemorrhagic lesions, were clinically ill and showed some mortality. The target cells are actively dividing B lymphocytes (Muller, 1986; Burkhardt and Muller, 1987). Muller (1986) demonstrated that IBDV will replicate preferentially in lymphoid cells from the bursa and poorly in lymphoid cells from other organs. It has been proposed that clinical signs of IBDV infection may result from immune complex formation (Ley et al., 1979; Skeeles et al., 1979). Muller (1986) however, demonstrated that the preferential replication in the lymphoid cells of the bursa is not related to the presence of surface immunoglobulins.

Two serotypes of IBDV, designated 1 and 2 have been demonstrated (McFerran et al., 1980; Jackwood et al., 1984; McNulty and Saif, 1988). Virulent serotypes have been shown in Group 1. No disease has been associated with group 2 viruses. In addition, considerable antigenic variation has been documented within serotypes (Lukert and Saif, 1991).

The causative agent, IBDV, has been classified as a Birnavirus (Brown et al., 1986). The biochemistry and replication of IBDV has been reviewed in Kibenge et al., (1988). Birnaviruses are small non-enveloped animal viruses having two segments of double-stranded RNA. The smaller genomic segment (segment B) of IBDV encodes a single polypeptide of 90k designated VP1. This protein is a minor internal component of the virion and is presumed to be the viral RNA polymerase (Hudson et al., 1986; Nagy et al., 1987; Spies et al., 1987). The larger genomic segment (segment A) encodes 5 polypeptides with the following designations and approximate molecular weights 52k (VPX), 41k (VP2), 32k (VP3), 28k (VP4) and 16k (Azad et al., 1985). The identity and presence of the 16K polypeptide has not been confirmed (Kibenge et al., 1988). VP2, VP3 and VP4 arise by co-translational proteolytic cleavage of precursor polyproteins. The protein VP4 is thought to be a viral protease (Hudson et al., 1986) responsible for cleavage between VPX and VP4 (Duncan et al., 1987) and between VP4 and VP3 (Azad et al., 1987; Jagadish et al., 1988).

Protein VP2 is the most abundant protein of the viral capsid making up 51% of serotype I IBDV proteins (Dobos et al., 1979). VP2 is only found in mature vital particles and is not seen in IBDV infected cells (Becht et al., 1988). VP2 is thought to be a specific cleavage product of a VPX precursor. Peptide mapping has shown that VPX and VP2 of IBDV strain CU-1 have similar amino acid sequences (Muller and Becht, 1982; Dobos, 979). In addition both VPX and VP2 react with the same monoclonal antibody on Western blots (Fahey et al., 1985b; Becht et al., 1988). It has recently been demonstrated that a conformational dependent neutralizing epitope exists on VP2 (Azad et al., 1987; Fahey et al., 1989) and a conformation independent neutralizing epitope exists on VP3 (Fahey et al., 1985 a,b). Antibodies to these epitopes were found to passively protect chickens (Fahey et al., 1985b; Azad et al., 1987; Fahey et al. 1989). Becht et al., (1988) and Snyder et al., (1988) indicated that neutralizing monoclonal antibodies to VP2 differentiated between serotypes 1 and 2 in cross-neutralization tests. However, Becht et al., (1988) also indicated that monoclonal antibodies to VP3 recognized a group-specific antigen from both serotypes which was not associated with neutralizing activity or protection. These studies may indicate the existence of multiple epitopes at least on VP2 and perhaps on VP3.

In a recent publication, Macreadie et al., (1990) demonstrated the expression of VP2 in a yeast vector. The size of the expressed protein was consistent with that of an authentic VP2. Centrifugation and gel filtration studies indicated that the VP2 expressed in yeast was in a high molecular weight aggregated form. Chickens inoculated with a crude extract of the yeast expressed VP2 developed an immune response as demonstrated by ELISA test and virus neutralization tests. One day old chickens were then inoculated with anti-sera from chickens previously inoculated with yeast expressed VP2. These chickens were passively protected against IBDV challenge as evidenced by lack of IBDV antigen in the bursa (Macreadie et al., 1990).

Current vaccination strategies against IBDV include both live and killed vaccines. Antibody transmitted from the hen via the yolk of the egg can protect chickens against early infections with IBDV. Therefore, use of killed vaccines in oil emulsions to stimulate high levels of maternal antibody is extensive in the field (Lukert and Saif, 1991). Studies by Lucio and Hitchner (1979) and Baxendale and Lutticken (1981) indicated that oil emulsion IBDV vaccines can stimulate adequate maternal immunity to protect chickens for 4–6 weeks. In contrast progeny from breeders vaccinated with live vaccines are protected for only 1–3 weeks after hatching (Lukert and Saif, 1991).

Determination of when maternal antibody has waned, and thus when antibody levels can be boosted by active immunization is problematical. It is therefore common practice to vaccinate all chicks against IBD with a live vaccine during the first 3 weeks of life (Winterfield et al., 1980). Inactivated vaccines are ineffective in inducing active immunity in chicks with maternal antibody. Presently available live vaccines consist of strains of intermediate virulence or highly attenuated strains, as well as some cell culture adapted variant strains. While intermediate strains can break through maternal antibody titers of approximately 1:250 (Lukert and Saif, 1991), the strains vary in virulence and can induce bursal atrophy and immunosuppression in day old and 3 week old SPF chickens (Lukert and Mazariegos, 1985).

Given the limitations of current vaccination strategies, it can be appreciated that provision of an IBDV recombinant poxvirus, and of vaccines which provide protective immunity against IBDV infections, would be a highly desirable advance over the current state of technology.

OBJECTS OF THE INVENTION

It is therefore an object of this invention to provide recombinant poxviruses, which viruses express gene products of IBDV, and to provide a method of making such recombinant poxviruses.

It is an additional object of this invention to provide for the cloning and expression of IBDV coding sequences, particularly sequences coding for IBDV structural proteins, in a poxvirus vector, particularly fowlpox virus.

It is another object of this invention to provide a vaccine which is capable of eliciting IBDV antibodies and protective immunity against IBDV infection.

These and other objects and advantages of the present invention will become more readily apparent after consideration of the following.

STATEMENT OF THE INVENTION

In one aspect, the present invention relates to a recombinant poxvirus containing therein a DNA sequence from IBDV in a nonessential region of the poxvirus genome. The poxvirus is advantageously an avipox virus, such as fowlpox virus.

According to the present invention, the recombinant poxvirus expresses gene products of the foreign IBDV gene. In particular, the foreign DNA codes for IBDV structural proteins. The IBDV gene may be co-expressed with other foreign genes in the host by the recombinant poxvirus.

In another aspect, the present invention relates to a vaccine for inducing an immunological response in a host animal inoculated with the vaccine, said vaccine including a carrier and a recombinant poxvirus containing, in a nonessential region thereof, DNA from IBDV. Advantageously, the DNA codes for and expresses IBDV structural proteins. The IBDV gene may be co-expressed with other foreign genes in the host. The poxvirus used in the vaccine according to the present invention is advantageously an avipox virus, such as fowlpox virus, referred to hereafter as TROVAC.

BRIEF DESCRIPTION OF THE DRAWINGS

A better understanding of the present invention will be had by referring to the accompanying drawing, in which:

FIG. 1 (SEQ. ID NO: 7) shows the nucleotide sequence of a 3661 base pair fragment of TROVAC DNA containing the F8 open reading frame.

September, 1989 where it was subjected to four successive plaque purifications. One plaque isolate was further amplified in primary CEF cells, and a stock virus, designated as TROVAC, established.

cDNA clones from IBDV strain Faragher (Type I) were obtained from Rhone Merieux, Lyon, France in June, 1990.

EXAMPLE 1

Construction of Insertion Vector for IBDV-VP2

Plasmid pIBDVA contains a 3.1 Kb KpnI to XbaI fragment derived from cDNA clones of IBDV strain Faragher. This fragment was inserted into vector pBluescript 11 SK+ (Stratagene, La Jolla, Calif.). The insert corresponds to the segment A of the IBDV genome which encodes the 108 kDa precursor polyprotein. The polyprotein is subsequently processed to form VP2, VP3 and VP4.

In order to isolate the coding sequence for VP2 from pIBDVA, VP3 and VP4 coding sequences were deleted from pIBDVA and a termination codon added to the 3' end of the VP2 coding sequence. This was accomplished by digestion of pIBDVA with ScaI and KpnI and insertion of the annealed and kinased oligonucleotides CE279 (SEQ ID NO:1) and 280 (SEQ ID NO:2) to form pCEN112.

CE279
```
ACTTCATGGAGGTGGCCGACCTCAACTCTCCCCTGAAGATTGCAGGAGCATTTGGCTTCA
AAGACATAATCCGGGCTATAAGGAGGTGAGTCGACGGTAC
```

CE280
```
CGTCGACTCACCTCCTTATAGCCCGGATTATGTCTTTGAAGCCAAATGCTCCTGCAATCT
TCAGGGGAGAGTTGAGGTCGGCCACCTCCATGAAGT
```

DETAILED DESCRIPTION OF THE INVENTION

The invention is directed to recombinant poxviruses containing therein a DNA sequence from IBDV in a nonessential region of the poxvirus genome. The recombinant poxviruses express gene products of the foreign IBDV gene. In particular, IBDV genes encoding IBDV structural proteins were isolated, characterized and inserted into TROVAC (FPV) recombinants.

Cell Lines and Virus Strains.

The strain of FPV designated FP-1 has been previously described (Taylor et al., 1988). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast (CEF) cells. This virus was obtained in September 1980 by Rhone Merieux, Lyon, France and a master vital seed established. The virus was received by Virogenetics in The vaccinia virus H6 promoter previously described in Taylor et al., (1988); Guo et al., (1989), Perkus et al., (1989), was inserted into pCEN112 by digesting pCEN112 with NotI, and blunt-ending with the Klenow fragment of DNA polymerase, in the presence of 10 mM dNTPs. A HindIII to EcoRV fragment which contains the H6 promoter was blunt-ended with the Klenow fragment of DNA polymerase and inserted into the linearized pCEN112 to generate pCEN117.

In order to align the ATG of the promoter with the initiating ATG of IBDV VP2 coding sequence, the annealed and kinased oligonucleotides CE277 (SEQ ID NO:3) and CE278 (SEQ ID NO:4) were inserted into pCEN117 that had been digested with NruI and RsrII. The resulting plasmid was designated pCEN120.

CE277
```
CGATATCATGACAAACCTGCAAGATCAAACCCAACAGATTGTTCCGTTCATACGGAGCCT
TCTGATGCCAACAACCG
```

CE278
```
GTCCGGTTGTTGGCATCAGAAGGCTCCGTATGAACGGAACAATCTGTTGGGTTTGATCTT
GCAGGTTTGTCATGATATCG
```

A SmaI to SalI fragment from pCEN120, containing IBDV-VP2 linked to the vaccinia virus H6 promoter was cloned into the HpaI and SalI sites of the FPV insertion vector pCEN100 (described below) to generate pCEN137.

Plasmid pCEN137 was used in an in vitro recombination test to generate recombinant vFP115.

EXAMPLE 2

Construction of Insertion Vector for IBDV VP2, VP3, VP4

Non-coding sequence was removed from the 3' end of the IBDV polyprotein sequence by partially digesting pIBDVA with PpuMI, completely digesting with KpnI, and re-inserting the annealed and kinased oligonucleotides CE275 (SEQ ID NO:5) and CE276 (SEQ ID NO:6) into pIBDVA to generate pCEN111.

CE275: GACCTTGAGTGAGTCGACGGTAC
CE276: CGTCGACTCACCTCAAG

A perfect 5' end to the polyprotein sequence was obtained in the following manner. A KpnI-BstEII fragment containing the majority of the polyprotein sequence with a perfect 3' end was excised from pCEN111 and ligated into the KpnI and BstEII sites of pCEN120. This substitution replaces the 3' end of the VP2 coding sequence and generates a perfect 5' end for the polyprotein with linkage to the vaccinia virus H6 promoter. The resulting plasmid was designated pCEN125.

The final insertion plasmid was constructed by partial digestion of pCEN125 with SmaI and complete digestion with SalI. The resulting fragment was cloned into the HpaI and SalI sites of pCEN100 (described below) to form pCEN138. Plasmid pCEN138 was used in an in vitro recombination test to generate recombinant vFP116.

EXAMPLE 3

Construction of Fowlpox Insertion Plasmid at F8 Locus

Plasmid pRW731.15 contains a 10 Kbp PvuII-PvuII fragment cloned from TROVAC genomic DNA. The nucleotide sequence was determined on both strands for a 3661 bp PvuII-EcoRV fragment. This sequence is shown in FIG. 1 (SEQ ID NO:7). The limits of an open reading frame designated in this laboratory as F8 were determined within this sequence. The open reading frame is initiated at position 929 and terminates at position 1888. In order not to interfere with neighboring open reading frames, the deletion was made from position 781 to position 1928, as described below.

Plasmid pRW761 is a sub-clone of pRW731.15 containing a 2430 bp EcoRV-EcoRV fragment. The F8 orf was entirely contained between an XbaI site and an SspI site in PRW761. In order to create an insertion plasmid which, on recombination with TROVAC genomic DNA would eliminate the F8 orf, the following steps were followed. Plasmid pRW761 was completely digested with XbaI and partially digested with SspI. A 3700 bp XbaI-SspI band was isolated and ligated with the annealed double-stranded oligonucleotides JCA017 (SEQ ID NO:8) and JCA018 (SEQ ID NO:9).

JCA017 5' CTAGACACTTTATGTTTTTTAATATCCGGTCTTAAAAGCTTCCCGGGGGATCCTT
ATACGGGGAATAAT 3'

JCA018 5' ATTATTCCCCGTATAAGGATCCCCCGGGAAGCTTTTAAGACCGGATATTAAAAAA
CATAAAGTGT 3'

The plasmid resulting from this ligation was designated pJCA002.

Additional cloning sites were incorporated into pJCA002 by inserting the annealed and kinased oligonucleotides CE205 (SEQ ID NO:10) and CE206 (SEQ ID NO:11) into the BamHI and HindIII sites of pJCA002 to form pCE72.

CE205: GATCAGAAAAACTAGCTAGCTAGTACGTAGTTAACGTCGACCTGCAGAAGCTTCT
AGCTAGCTAGTTTTTAT

CE206: AGCTATAAAAACTAGCTAGCTAGAAGCTTCTGCAGGTCGACGTTAACTACGTACT
AGCTAGCTAGTTTTTCT

In order to increase the length of the FPV flanking arms in the insertion plasmid, plasmid pJCA021 was constructed. Plasmid pJCA021 was obtained by inserting a 4900bp PvuII-HindII fragment from pRW 731-15 (previously described) into the SmaI and HindII sites of pBluescript SS K⁺(Stratagene, La Jolla, Calif.). A BglII to EcoRI fragment from pCEN72 was then ligated into the BglII and EcoRI sites of pJCA021 to generate pCEN100.

EXAMPLE 4

Development of Trovac-IBDV Recombinants

Plasmids pCEN137 and pCEN138 were transfected into TROVAC infected primary CEF cells by using the calcium phosphate precipitation method previously described (Panicali and Paoletti, 1982; Piccini et al., 1987). Positive plaques were selected on the basis of hybridization to specific IBDV radiolabeled probes and subjected to five sequential rounds of plaque purification until a pure population was achieved. One representative plaque from each IVR was then amplified and the resulting TROVAC recombinants were designated vFP115 (IBDV-VP2) and vFP116 (IBDV-VP2, VP3, VP4).

Immunofluorescence.

In order to determine where the IBDV proteins were localized in recombinant infected CEF cells, immunofluorescence analysis was performed. Indirect immunofluorescence was performed was performed as described in Taylor et al., (1990) using a neutralizing monoclonal antibody preparation designated AC6 obtained from Rhone Merieux in July 1990 and a polyclonal chicken anti-IBDV serum obtained from Spafas Inc., Storrs, Conn.

The results indicated that IBDV specific immunofluorescence could be detected in the cytoplasm of cells infected with either vFP115 or vFP116 . No fluorescence was detected in parental TROVAC infected CEF cells. No surface fluorescence was detected in cells infected with either recombinant virus. Equivalent results were obtained using both the neutralizing monoclonal antibody preparation and the polyclonal immune serum. The result was not unexpected since the analysis of the sequence of the IBDV genes does not indicate the presence of characteristic signal and anchor sequences which would direct insertion of the proteins in the infected cell membrane.

Immunoprecipitation.

Immunoprecipitation reactions were performed as described in Taylor et al., (1990) using the neutralizing monoclonal antibody preparation and the polyclonal anti-IBDV immune serum from,chickens as described above.

Immunoprecipitation analysis of CEF cells infected with recombinant vFP115 indicated the expression of a protein of approximately 38–40 Kd recognized by both polyclonal immune sera and the neutralizing monoclonal antibody. This size is appropriate for expression of the structural protein, VP2 (Azad et al., 1985). Immunoprecipitation analysis of lysates of cells infected with recombinant vFP116 encoding the IBDV polyprotein also demonstrated expression of a single protein species of approximately 43 Kd. This protein is recognized by botch polyclonal immune serum and the neutralizing monoclonal antibody preparation. Both the size of the protein and its recognition by the monoclonal antibody indicate that the identity of this protein may be VPX, the precursor to VP2. Although no other proteins are immunoprecipitation by the immune serum, presence of the cleaved VPX indicates that VP4, the cleavage protein is probably expressed. Since VP4 is a very minor component of the virion, it is not unusual that the immune serum should not contain antibodies to this protein.

No conclusions can be drawn on expression of VP3. This protein comprises 40% of the virion and therefore it is likely that antibodies to the protein would be present in immune serum. Restriction analysis of genomic DNA derived from the recombinant indicate that no gross deletions have occurred on insertion of the polyprotein coding sequences.

EXAMPLE 5

Immunization of Chickens and Subsequent Challenge

Groups of 20, 5 day old susceptible SPF chickens were inoculated by subcutaneous injection in the nape of the neck with 0.2 ml of recombinants vFP115 or vFP116. This corresponded to a dose of approximately 4.0 log$_{10}$ TCID$_{50}$. A group of 19 birds were left as uninoculated controls. At fourteen days post vaccination, chickens were bled and serum neutralizing titers in the sera were determined. Birds were challenged at 14 days by intra-ocular inoculation of 0.03ml of the virulent serotype I IBDV challenge strain supplied by the USDA National Veterinary Services Laboratory. Five days after challenge, each chicken was necropsied and the bursa examined for gross lesions and the appearance of atrophy.

The results are shown in Table 1.

The results indicate that inoculation of one dose of vFP115 expressing the VP2 structural protein leads to the induction of serum neutralizing antibody and 75% protection of challenged birds. Inoculation of vFP116 leads to the induction of a poor neutralizing antibody response but 50% of Challenged birds are protected.

TABLE 1

| Protective Efficacy of TROVAC-IBDV Recombinants in Chickens | | | |
|---|---|---|---|
| Recombinant | # Protected/Challenged[b] | % Protection | SN Titer[a] |
| vFP115 | 15/20 | 75 | 131 |
| vFP116 | 10/19 | 53 | 6 |
| Controls | 0/19 | 0 | 0 | a: Serum neutralization titer
b: Birds are considered protected in the absence of bursal atrophy and lesions.

EXAMPLE 6

IBDV Recombinant Poxvirus Vaccines

Recombinant poxviruses containing, in a nonessential region thereof, DNA from IBDV provide advantages as vaccines for inducing an immunological response in a host animal. Infectious bursal disease virus is very stable and persists in the environment for long periods. For economic reasons, poultry houses are rarely cleaned between broods and thus chickens are exposed to the virus early in life. Since elimination of virus by hygienic means is not possible, vaccination strategies need to be formed. Active immunization of chickens is difficult in the presence of maternal antibody. In addition, since maternal antibody levels are variable and the rate of loss of antibody unpredictable, timing of vaccination is a problem. A successful vaccine will need to be able to boost immunity in the presence of maternal antibody and should also contain cross-reactive antigens from a number of different serotypes. In addition, an effective vaccine should not induce signs of disease in vaccinated birds.

TROVAC-IBDV recombinant vFP115 expressed the major structural protein VP2 Which has been shown to contain at least one highly immunogenic region. The protein expressed by the TROVAC recombinant is recognizable by IBDV immune serum. Inoculation of this recombinant into susceptible birds-resulted in 75% protection from bursal damage. Recombinant vFP116 contains the coding sequence for the polyprotein VP2, VP3, VP4. A protein probably corresponding to VPX, the VP2 precursor, was expressed which is also recognized by IBDV immune sera. Inoculation of this recombinant into susceptible birds lead to the development of low neutralizing antibody levels, but induced 53% protection from bursal damage.

The results indicate the potential of TROVAC-IBDV recombinants for vaccination against IBDV in the poultry industry. The restricted host range of FPV provides an inherent safety barrier to transmission of recombinant to non-vaccinated species. Use of antigenic regions of IBDV rather than whole virus eliminates the need to introduce live virus to the environment and may lessen the immunological pressure on the virus which leads to the emergence of variant strains. The large size of the FPV genome allows incorporation of multiple antigenic sequences and should allow for vaccination against a variety of strains.

References

1. Allan, W. H., J. T. Faragher, and G. A. Cullen, Vet. Rec. 90, 511–512 (1972).

2. Azad, A. A., S. A. Barrett, and K. J. Fahey, Virology 143,35–44 (1985).
3. Azad, A. A., K. J. Fahey, S. Barrett, K. Erny and P. Hudson, Virology 149, 190–198 (1986).
4. Azad, A. A., M. N. Jagadish, M. A. Brown, and P. J. Hudson, Virology 161, 145–152 (1987).
5. Baxendale, W. and Lutticken, Dev. Biol. Stand. 51, 211–219 (1931).
6. Becht, H., H. Muller, and H. K. Muller, J. Gen. Virol. 69, 631–640 (1988).
7. Brown, F., Intervirology 25, 141–143 (1986).
8. Burkhardt, E. and H. Muller, Archives of Virology 94, 297–303 (1937).
9. Clewell, D. B., J. Bacteriol. 110, 667–676 (1972).
10. Clewell, D. B. and D. R. Helinski, Proc. Natl. Acad. Sci. USA 62, 1159–1166 (1969).
11. Dobos, P., J. Virol. 32, 1046–1050 (1979).
12. Dobos, P., B. J. Hill, R. Hallett, D. T. Kells, H. Becht, and D. Teninges, J. Virol. 32, 593–605 (1979).
13. Duncan, R., E. Nagy, P. J. Krell and P. Dobos, J. Virol. 61, 3655–3664 (1987).
14. Edbauer, C., R. Weinberg, J. Taylor, A. Rey-Senelonge, J. F. Bouquet, P. Desmettre and E. Paoletti, Virology 179, 901–904 (1990).
15. Fahey, K. J., I. J. O'Donnell, and A. A. Azad, J. Gen. Virol. 66, 1479–1488 (1985a).
16. Fahey, K. J., I. J. O'Donnell, and T. J. Bagust, J. Gen. Virol. 66, 2693–2702 (1985b).
17. Fahey, K. J., K. Erny and J. Crooks, J. Gen. Virol. 70, 1473–1481 (1989).
18. Guo, P., S. Goebel, S. Davis, M. E. Perkus, B. Languet, P. Desmettre, G. Allen, and E. Paoletti, J. Virol. 63, 4189–4198 (1989).
19. Hudson, P. J., N. M. McKern, B. E. Power, and A. A. Azad, Nucl. Acids. Res. 14, 5001–5012 (1986).
20. Jackwood, D. J., Y. M. Saif, and J. H. Hughes, Avian Dis. 28, 990–1006 (1984).
21. Jagadish, M. N., V. J. Staton, P. J. Hudson, and A. A. Azad, J. Virol. 62, 1084–1087 (1988).
22. Kaufer, I. and E. Weiss, Infect. Immun. 27, 364–367 (1980).
23. Kibenge, F. S. B., A. S. Dhillon, and R. G. Russell, J. Gen. Virol. 69, 1757–1775 (1988).
24. Ley, D. H., R. Yamamoto, and A. A. Bickford, Avian Diseases 23, 219–224 (1979).
25. Lucio, B. and S. B. Hitchner, Avian Dis. 23, 466–478 (1979).
26. Lukert, P. D. and S. B. Hitchner, In Diseases of Poultry 8th edition, eds. M. S. Hofstad, H. J. Barnes, B. W. Calnek, W. M. Reid and H. W. Yoder (Iowa State University Press-Ames) pp. 566–576 (1984).
27. Lukert, P. D. and L. A. Mazariegos, J. Am. Vet. Med. Assoc. 187, 306 (ABSTR).
28. Lukert, P. D. and Y. M. Saif, In Diseases of Poultry 9th edition, eds. B. W. Calnek, H. J. Barnes, C. W. Beard, W. M. Reid and H. W. Yoder (Iowa State University Press-Ames) pp. 648–663 (1991).
29. Macreadie, I. G., P. R. Vaughan, A. J. Chapman, N. M. McKern, M. N. Jagadish, H. G. Heine, C. W. Ward, K. J. Fahey, and A. A. Azad, Vaccine 8, 549–552 (1990).
30. Matthews, R. E. F., Intervirology 17, 42–44 (1982).
31. McFerran, J. B., M. S. McNulty, E. R. McKillop, T. J. Connor, R. M. McCracken, D. S. Collins, and G. M. Allen, Avian Pathol. 9, 395–404 (1980).
32. McNulty, M. S. and Y. M. Saif, Avian Dis. 32, 374–375 (1988).
33. Muller, H., Arch. Virol. 87, 191–203 (1986).
34. Muller, H. and H. Betch, J. Virol. 44, 384–392 (1982).
35. Nagy, E., R. Duncan, P. Krell, and P. Dobos, Virology 158, 211–217 (1987).
36. Panicali, D. and E. Paoletti, Proc. Natl. Acad. Sci. USA 79, 4927–4931 (1982).
37. Perkus, M. E., K. Limbach, and E. Paoletti, J. Virol. 63, 3829–3836 (1989).
38. Piccini, A., M. E. Perkus, and E. Paoletti, In Methods in Enzymology, Vol. 153, eds. Wu, R., and Grossman, L., (Academic Press) pp. 545–563 (1987).
39. Sambrook, J., E. F. Fritsch, and T. Maniatis, In Molecular cloning: A laboratory manual, 2nd edition, (Cold Spring Harbor Press, NY) (1989).
40. Schat, K. A., B. Lucio, and J. C. Carlisle, Avian Dis. 25, 996–1004 (1981).
41. Skeeles, J. K., P. D. Lukert, E. V. De Buysscher, O. J. Fletcher, and J. Brown, Avian Dis. 23, 95–106 (1979).
42. Snyder, D. B., D. P Lana, B. R. Cho, and W. W. Marquardt, Avian Dis. 32, 527–534 (1988).
43. Spies, U., H. Muller, and H. Becht, Virus Res. 8, 127–140 (1987).
44. Taylor, J., C. Edbauer, A. Rey-Senelonge, J. F. Bouquet, E. Norton, S. Goebel, P. Desmettre and E. Paoletti, J. Virol. 64, 1441–1450 (1990).
45. Taylor, J., R. Weinberg, Y. Kawaoka, R. Webster and E. Paoletti, Vaccine 6, 504–508 (1988).
46. Winterfield, R. W., A. S. Dhillon, H. L. Thacker, L. J. Alby, Avian Dis. 24, 179–188 (1980).

---

What is claimed is:

1. A recombinant avipox virus containing in a nonessential region of the avipox virus genome, DNA from infectious bursal disease virus which codes for and is expressed as infectious bursal disease virus structural polyprotein VP2, VP3, VP4, wherein the recombinant avipox virus induces an immunological response in a host animal inoculated therewith.

2. A recombinant avipox virus as in claim 1 wherein the avipox virus is fowlpox virus.

3. The recombinant avipox virus of claim 1 which is a fowlpox virus which has attenuated virulence through approximately 50 serial passages on chicken embryo fibroblast cells, then subjecting the fowlpox virus to four successive plaque purifications, and obtaining a plaque isolate and further amplifying the isolate in primary chick embryo fibroblast cells.

4. An immunological composition for inducing an immunological response in a host inoculated with the immunological composition, said immunological composition comprising a carrier and the recombinant avipox virus of claim 3.

5. A method for inducing an immunological response in a host comprising administering to the host the immunological composition of claim 4.

6. The method of claim 5 wherein the host is a chicken.

7. A immunological composition for inducing an immunological response in a host animal inoculated with said immunological composition, said immunological composition comprising a carrier and a recombinant avipox virus containing, in a nonessential region thereof, DNA from infectious bursal disease virus which codes for and is expressed as VP2, VP3, VP4, infectious bursal disease virus structural polyprotein.

8. An immunological composition as in claim 7 wherein the avipox virus is fowlpox virus.

9. A method for inducing an immunological response in a host comprising administering to the host the immunological composition of claim 7.

10. The method of claim 9 wherein the host is a chicken.

* * * * *

UNITED STATES PATENT AND TRADEMARK OFFICE
CERTIFICATE OF CORRECTION

PATENT NO. : 5,658,572
DATED : August 19, 1997
INVENTOR(S) : Paoletti et al.

Page 1 of 2

It is certified that error appears in the above-indentified patent and that said Letters Patent is hereby corrected as shown below:

At Column 5, line 25: after "FIG. 1" insert --(FIGS. 1A, 1B, 1C)--.

At Column 6, line 4: after "established" insert --TROVAC was deposited under the terms of the Budapest Treaty with the American Type Culture Collection (ATCC), 12301 Parklawn Drive, Rockville, Maryland 20852, USA, ATCC accession number VR-2553.--

IN THE CLAIMS:

Claim 3, line 2: before "fowlpox virus" insert --TROVAC fowlpox virus or a--.

Claim 7, line 1: change "A" to --An--.

Claim 7, line 7: change "expressed as VP2, VP3, VP4 infectious bursal disease virus structural polyprotein." to --expressed as infectious bursal disease virus structural polyprotein VP2, VP3, VP4.--

UNITED STATES PATENT AND TRADEMARK OFFICE
CERTIFICATE OF CORRECTION

PATENT NO. : 5,658,572
DATED : August 19, 1997
INVENTOR(S) : Paoletti et al.

It is certified that error appears in the above-identified patent and that said Letters Patent is hereby corrected as shown below:

Add Claim 11 as follows:

--11. The recombinant avipox virus of Claim 3 which is vFP116.--

Signed and Sealed this

Twenty-fourth Day of February, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ACTTCATGGA  GGTGGCCGAC  CTCAACTCTC  CCCTGAAGAT  TGCAGGAGCA  TTTGGCTTCA        60
```

AAGACATAAT CCGGGCTATA AGGAGGTGAG TCGACGGTAC 100

( 2 ) INFORMATION FOR SEQ ID NO:2:

( i ) SEQUENCE CHARACTERISTICS:
    ( A ) LENGTH: 96 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

CGTCGACTCA CCTCCTTATA GCCCGGATTA TGTCTTTGAA GCCAAATGCT CCTGCAATCT 60

TCAGGGGAGA GTTGAGGTCG GCCACCTCCA TGAAGT 96

( 2 ) INFORMATION FOR SEQ ID NO:3:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

CGATATCATG ACAAACCTGC AAGATCAAAC CCAACAGATT GTTCCGTTCA TACGGAGCCT 60

TCTGATGCCA ACAACCG 77

( 2 ) INFORMATION FOR SEQ ID NO:4:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

GTCCGGTTGT TGGCATCAGA AGGCTCCGTA TGAACGGAAC AATCTGTTGG GTTTGATCTT 60

GCAGGTTTGT CATGATATCG 80

( 2 ) INFORMATION FOR SEQ ID NO:5:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

GACCTTGAGT GAGTCGACGG TAC 23

( 2 ) INFORMATION FOR SEQ ID NO:6:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

CGTCGACTCA CTCAAG 16

( 2 ) INFORMATION FOR SEQ ID NO:7:

( i ) SEQUENCE CHARACTERISTICS:
    ( A ) LENGTH: 3661 base pairs
    ( B ) TYPE: nucleic acid
    ( C ) STRANDEDNESS: single -continued (D) TOPOLOGY: linear (xi) SEQUENCE DESCRIPTION: SEQ ID NO:7:

| | | | | | |
|---|---|---|---|---|---|
| GATATCTGTG | GTCTATATAT | ACTACACCCT | ACCGATATTA | ACCAACGAGT | TTCTCACAAG | 60 |
| AAAACTTGTT | TAGTAGATAG | AGATTCTTTG | ATTGTGTTTA | AAAGAAGTAC | CAGTAAAAAG | 120 |
| TGTGGCATAT | GCATAGAAGA | AATAAACAAA | AAACATATTT | CCGAACAGTA | TTTTGGAATT | 180 |
| CTCCCAAGTT | GTAAACATAT | TTTTGCCTA | TCATGTATAA | GACGTTGGGC | AGATACTACC | 240 |
| AGAAATACAG | ATACTGAAAA | TACGTGTCCT | GAATGTAGAA | TAGTTTTTCC | TTTCATAATA | 300 |
| CCCAGTAGGT | ATTGGATAGA | TAATAAATAT | GATAAAAAA | TATTATATAA | TAGATATAAG | 360 |
| AAAATGATTT | TTACAAAAAT | AACCTATAAG | AACAATAAAA | ATATAATTAC | ATTTACGGAA | 420 |
| AATAGCTGGT | TTTAGTTTAC | CAACTTAGAG | TAATTATCAT | ATTGAATCTA | TATTGTTTTT | 480 |
| TAGTTATATA | AAAACATGAT | TAGCCCCCAA | TCGGATGAAA | ATATAAAGA | TGTTGAGAAT | 540 |
| TTCGAATACA | ACAAAAGAG | GAATCGTACG | TTGTCCATAT | CCAAACATAT | AAATAAAAAT | 600 |
| TCAAAAGTAG | TATTATACTG | GATGTTTAGA | GATCAACGTG | TACAAGATAA | TTGGGCTTTA | 660 |
| ATTTACGCAC | AACGATTAGC | GTTAAAACTC | AAAATACCTC | TAAGAATATG | CTTTTGTGTC | 720 |
| GTGCCAAAAT | TTCACACTAC | TACTTCTAGT | ACACTTTATG | TTTTTAATAT | CCGGTCTTAA | 780 |
| AGAAGTCGCG | GAAGAATGTA | AAAGACTATG | TATAGGGTTT | TCATTGATAT | ATGGCGTACC | 840 |
| AAAAGTAATA | ATTCCGTGTA | TAGTAAAAAA | ATACAGAGTC | GGAGTAATCA | TAACGGATTT | 900 |
| CTTTCCATTA | CGTGTTCCCG | AAAGATTAAT | GAAACAGACT | GTAATATCTC | TTCCAGATAA | 960 |
| CATACCTTTT | ATACAAGTAG | ACGCTCATAA | TATAGTACCT | TGTTGGGAAG | CTTCTGATAA | 1020 |
| AGAAGAATAC | GGTGCACGAA | CTTTAAGAAA | AAAGATATTT | GATAAATTAT | ATGAATATAT | 1080 |
| GACAGAATTT | CCTGTTGTTC | GTAAACATCC | ATACGGTCCA | TTTTCTATAT | CTATTGCAAA | 1140 |
| ACCCAAAAAT | ATATCATTAG | ACAAGACGGT | ATTACCCGTA | AAATGGGCAA | CGCCTGGAAC | 1200 |
| AAAAGCTGGA | ATAATTGTTT | TAAAAGAATT | TATAAAAAAC | AGATTACCGT | CATACGACGC | 1260 |
| GGATCATAAC | AATCCTACGT | GTGACGCTTT | GAGTAACTTA | TCTCCGTGGC | TACATTTTGG | 1320 |
| TCATGTATCC | GCACAACGTG | TTGCCTTAGA | AGTATTAAAA | TGTATACGAG | AAAGCAAAAA | 1380 |
| AAACGTTGAA | ACGTTTATAG | ATGAAATAAT | TGTAAGAAGA | GAACTATCGG | ATAATTTTTG | 1440 |
| TTACTATAAC | AAACATTATG | ATAGTATCCA | GTCTACTCAT | TCATGGGTTA | GAAAAACATT | 1500 |
| AGAAGATCAC | ATTAATGATC | CTAGAAAGTA | TATATATTCC | ATTAAACAAC | TCGAAAAAGC | 1560 |
| GGAAACTCAT | GATCCTCTAT | GGAACGCGTC | ACAAATGCAG | ATGGTGAGAG | AAGGAAAAAT | 1620 |
| GCATAGTTTT | TTACGAATGT | ATTGGGCTAA | GAAGATACTT | GAATGGACTA | GAACACCTGA | 1680 |
| AGACGCTTTG | AGTTATAGTA | TCTATTTGAA | CAACAAGTAC | GAACTAGACG | GCACGGATCC | 1740 |
| TAACGGATAC | GTAGGTTGTA | TGTGGTCTAT | TTGCGGATTA | CACGATAGAG | CGTGGAAAGC | 1800 |
| AAGACCGATA | TTTGGAAAGA | TAAGATATAT | GAATTATGAG | AGTTCTAAGA | AGAAATTTGA | 1860 |
| TGTTGCTGTA | TTTATACAGA | AATACAATTA | AGATAAATAA | TATACAGCAT | TGTAACCATC | 1920 |
| GTCATCCGTT | ATACGGGGAA | TAATATTACC | ATACAGTATT | ATTAAATTTT | CTTACGAAGA | 1980 |
| ATATAGATCG | GTATTTATCG | TTAGTTTATT | TTACATTTAT | TAATTAAACA | TGTCTACTAT | 2040 |
| TACCTGTTAT | GGAAATGACA | AATTTAGTTA | TATAATTTAT | GATAAAATTA | AGATAATAAT | 2100 |
| AATGAAATCA | AATAATTATG | TAAATGCTAC | TAGATTATGT | GAATTACGAG | GAAGAAAGTT | 2160 |
| TACGAACTGG | AAAAAATTAA | GTGAATCTAA | AATATTAGTC | GATAATGTAA | AAAAAATAAA | 2220 |
| TGATAAAACT | AACCAGTTAA | AAACGGATAT | GATTATATAC | GTTAAGGATA | TTGATCATAA | 2280 |

| | | | | | |
|---|---|---|---|---|---|
| AGGAAGAGAT | ACTTGCGGTT | ACTATGTACA | CCAAGATCTG | GTATCTTCTA | TATCAAATTG | 2340 |
| GATATCTCCG | TTATTCGCCG | TTAAGGTAAA | TAAAATTATT | AACTATTATA | TATGTAATGA | 2400 |
| ATATGATATA | CGACTTAGCG | AAATGGAATC | TGATATGACA | GAAGTAATAG | ATGTAGTTGA | 2460 |
| TAAATTAGTA | GGAGGATACA | ATGATGAAAT | AGCAGAAATA | ATATATTTGT | TTAATAAATT | 2520 |
| TATAGAAAAA | TATATTGCTA | ACATATCGTT | ATCAACTGAA | TTATCTAGTA | TATTAAATAA | 2580 |
| TTTTATAAAT | TTTATAAATT | TTAATAAAAA | ATACAATAAC | GACATAAAGA | TATTTAATCT | 2640 |
| TTAATTCTTG | ATCTGAAAAA | CACATCTATA | AAACTAGATA | AAAGTTATT | CGATAAAGAT | 2700 |
| AATAATGAAT | CGAACGATGA | AAAATTGGAA | ACAGAAGTTG | ATAAGCTAAT | TTTTTTCATC | 2760 |
| TAAATAGTAT | TATTTTATTG | AAGTACGAAG | TTTTACGTTA | GATAAATAAT | AAAGGTCGAT | 2820 |
| TTTTACTTTG | TTAAATATCA | AATATGTCAT | TATCTGATAA | AGATACAAAA | ACACACGGTG | 2880 |
| ATTATCAACC | ATCTAACGAA | CAGATATTAC | AAAAAATACG | TCGGACTATG | GAAAACGAAG | 2940 |
| CTGATAGCCT | CAATAGAAGA | AGCATTAAAG | AAATTGTTGT | AGATGTTATG | AAGAATTGGG | 3000 |
| ATCATCCTCA | ACGAAGAAAT | AGATAAAGTT | CTAAACTGGA | AAAATGATAC | ATTAAACGAT | 3060 |
| TTAGATCATC | TAAATACAGA | TGATAATATT | AAGGAAATCA | TACAATGTCT | GATTAGAGAA | 3120 |
| TTTGCGTTTA | AAAAGATCAA | TTCTATTATG | TATAGTTATG | CTATGGTAAA | ACTCAATTCA | 3180 |
| GATAACGAAC | ATTGAAAGAT | AAAATTAAGG | ATTATTTTAT | AGAAACTATT | CTTAAAGACA | 3240 |
| AACGTGGTTA | TAAACAAAAG | CCATTACCCG | GATTGGAAAC | TAAAATACTA | GATAGTATTA | 3300 |
| TAAGATTTTA | AAAACATAAA | ATTAATAGGT | TTTTATAGAT | TGACTTATTA | TATACAATAT | 3360 |
| GGATAAAAGA | TATATATCAA | CTAGAAAGTT | GAATGACGGA | TTCTTAATTT | TATATTATGA | 3420 |
| TTCAATAGAA | ATTATTGTCA | TGTCGTGTAA | TCATTTTATA | AATATATCAG | CGTTACTAGC | 3480 |
| TAAGAAAAAC | AAGGACTTTA | ATGAATGGCT | AAAGATAGAA | TCATTTAGAG | AAATAATAGA | 3540 |
| TACTTTAGAT | AAAATTAATT | ACGATCTAGG | ACAACGATAT | TGTGAAGAAC | TTACGGCGCA | 3600 |
| TCACATTCCA | GTGTAATTAT | TGAGGTCAAA | GCTAGTAACT | TAATAGATGA | CAGGACAGCT | 3660 |
| G | | | | | | 3661 |

( 2 ) INFORMATION FOR SEQ ID NO:8:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

| | | | | | |
|---|---|---|---|---|---|
| CTAGACACTT | TATGTTTTTT | AATATCCGGT | CTTAAAAGCT | TCCCGGGGGA | TCCTTATACG | 60 |
| GGGAATAAT | | | | | | 69 |

( 2 ) INFORMATION FOR SEQ ID NO:9:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

| | | | | | |
|---|---|---|---|---|---|
| ATTATTCCCC | GTATAAGGAT | CCCCCGGGAA | GCTTTTAAGA | CCGGATATTA | AAAAACATAA | 60 |
| AGTGT | | | | | | 65 |

( 2 ) INFORMATION FOR SEQ ID NO:10:

( i ) SEQUENCE CHARACTERISTICS:
  ( A ) LENGTH: 72 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:10:

```
GATCAGAAAA ACTAGCTAGC TAGTACGTAG TTAACGTCGA CCTGCAGAAG CTTCTAGCTA    60

GCTAGTTTTT AT                                                        72
```

( 2 ) INFORMATION FOR SEQ ID NO:11:

( i ) SEQUENCE CHARACTERISTICS:
  ( A ) LENGTH: 72 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:11:

```
AGCTATAAAA ACTAGCTAGC TAGAAGCTTC TGCAGGTCGA CGTTAACTAC GTACTAGCTA    60

GCTAGTTTTT CT                                                        72
```